(12) United States Patent
Imai

(10) Patent No.: US 8,057,417 B2
(45) Date of Patent: Nov. 15, 2011

(54) LOWER BACK SUPPORTER

(75) Inventor: Masayuki Imai, Okayama (JP)

(73) Assignees: Daiya Industry Co., Ltd.,
Okayama-Ken (JP); Masayuki Imai,
Okayama-Ken (JP)

( * ) Notice: Subject to any disclaimer, the term of this patent is extended or adjusted under 35 U.S.C. 154(b) by 194 days.

(21) Appl. No.: 12/381,202

(22) Filed: Mar. 9, 2009

(65) Prior Publication Data
US 2010/0228170 A1    Sep. 9, 2010

(51) Int. Cl.
*A61F 5/00* (2006.01)
*A61F 5/28* (2006.01)

(52) U.S. Cl. ............ 602/19; 128/100.1; 128/101.1

(58) Field of Classification Search ......... 602/5, 19,
602/60–61, 67; 128/96.1, 99.1, 100.1, 101.1,
128/102.1, 876; 2/44, 311–312, 321–322,
2/338, 467; 450/119, 137; D24/190; D2/627
See application file for complete search history.

(56) References Cited

U.S. PATENT DOCUMENTS

| | | | | |
|---|---|---|---|---|
| 2,117,309 A * | 5/1938 | Fritsch | ............ | 602/19 |
| 2,476,029 A * | 7/1949 | Dawson | ............ | 450/138 |
| 3,754,549 A * | 8/1973 | Nelkin | ............ | 128/100.1 |
| 3,926,183 A * | 12/1975 | Spiro | ............ | 602/19 |
| 4,245,628 A * | 1/1981 | Eichler | ............ | 602/19 |
| 4,794,916 A * | 1/1989 | Porterfield et al. | ............ | 602/19 |
| 5,500,959 A * | 3/1996 | Yewer, Jr. | ............ | 602/19 |
| 5,722,940 A * | 3/1998 | Gaylord et al. | ............ | 602/19 |
| 5,853,378 A * | 12/1998 | Modglin | ............ | 602/19 |
| 7,449,006 B2 * | 11/2008 | Wolanske | ............ | 602/19 |
| 2009/0326427 A1 * | 12/2009 | Kawahara | ............ | 602/19 |

FOREIGN PATENT DOCUMENTS

| JP | S62-186716 | 11/1987 |
|---|---|---|
| JP | H11-104159 | 4/1999 |
| JP | 2009017932 A * | 1/2009 |

OTHER PUBLICATIONS

Ikuei Yamamoto et al., "Practice and Theory of Taping from the Perspective of Sports . . . ", Apr. 21, 1997, Fourth Edition, pp. 216-217, Bunkodo Corp.
Setsuro Kuriyama, "New Taping Practicalities", Mar. 1, 1998, Second Printing, pp. 124-127, Nankodo Corp.

* cited by examiner

*Primary Examiner* — Patricia Bianco
*Assistant Examiner* — Kari Petrik
(74) *Attorney, Agent, or Firm* — DLA Piper LLP (US)

(57) ABSTRACT

A lower back supporter including a pair of flat anchor parts that come into contact with the lower back of a wearer with a specified space in between, a pair of anchor belts that wrap around the abdomen with the end portions connected to each other, a first and second support belt that cross over each other on the back, and a connecting belt that connects the anchor parts. The inner side surface of the anchor part comprising a non-slip material that closely contacts the skin of the wearer, and the outer side surface comprising a material that fastens to surface fasteners. After the anchor belts are put on, operation belts connected to the first and second support belts are pulled, the surface fasteners are fastened to the outer side surfaces of the anchor parts, applying tensile force between the anchor parts in closely contact to the lower back.

6 Claims, 10 Drawing Sheets

LOWER BACK SUPPORTER

BACKGROUND OF THE INVENTION

1. Field of the Invention

The present invention relates to a new lower back supporter alternative to a known lower back taping which is used for reducing and preventing recurrence of lower back pain.

2. Description of the Related Art

In lower back taping, a tape that is made of cotton or chemical fiber or the like with an adhesive agent on its one surface is used, and the tape is applied diagonally and horizontally to the back of a patient from the sides to the center of the back so that it puts pressure on the lower back and supports, restricts and immobilizes the lower back, thus dispersing the impact applied to the lower back to reduce and prevent recurrence of lower back pain. Recently, taping has come to be used widely in particularly the sports field for the purpose of preventing injuries and for fast function recovery training or participation in games and the like (see "Practice and Theory of Taping from the Perspective of Sports Injuries and Damage," written by Yamamoto and Hirakawa and published by Bunkodo Corp. on Apr. 21, 1997, Fourth Edition, Second Printing, pages 216 to 217; and "New Taping Practicalities," written by Kuriyama and published by Nankodo Corp. on Mar. 1, 1998, Second Printing, pages 124 to 127).

Meanwhile, supporters worn around the lower back for the same purpose as of the taping are also known (see Japanese Patent Application Laid-Open (Kokai) No. H11-104159 and Japanese Utility Model Application Laid-Open (Kokai) No. S62-186716).

However, the tape used in taping has problems. It is difficult to handle when it is being applied because of its adhesiveness, and a rash would occur on the skin of a wearer due to the adhesive agent depending on the physical constitution of the patient. In addition, tape removed from the body cannot be reused and has to be disposed of, and thus new tape is required with each application, and further it is necessary to have the tape applied by an expert.

Meanwhile, lower back supporters generally do not have the problems mentioned above and can be easily put on. However, since these supporters are of a type that may increase abdominal pressure to stabilize the lower back, there is a strong sensation of pressure on the abdomen, and the problem is that such supporters are uncomfortable and painful to wear for a long time, and they can slip easily while being worn (they can slip easily especially upward).

BRIEF SUMMARY OF THE INVENTION

The present invention is created taking into consideration of the problems described above with the conventionally lower back taping and lower back supporter, and it is an object of the present invention to provide a new lower back supporter which, while having the same function as conventional taping, does not have the above-described problems specific to taping and is as easy to wear as in a conventional lower back supporter, but is not uncomfortable to wear for a long time, and further is prevented from slipping while it is being worn.

The lower back supporter of the present invention comprises: a pair of flat first and second anchor parts of which inner side surfaces comprising a non-slip material which closely contacts a skin of a wearer and of which outer side surfaces comprising a material to which a surface fastener is fastened, the pair of anchor parts coming into contact with a lower back of the wearer with a specified space in between; a pair of anchor belts connected respectively to the pair of anchor parts and brought to an abdomen side of the wearer so that end portions of the anchor belts are coupled to each other; a first support belt connected to the first anchor part and brought to the second anchor part through a central back side so that the first support belt is fastened to the outer side surface of the second anchor part via a surface fastener; and a second support belt connected to the second anchor part and brought to the first anchor part through the central back side of the wearer so that the second support belt is fastened to the outer side surface of the first anchor part.

When this supporter is worn, the pair of anchor parts are brought to come into contact almost laterally in a symmetric manner with suitable positions ranging from the sides of the waist to the central back area of a wearer, though the pair of anchor belts can be omitted.

The above-described lower back supporter can be further comprised of a center connecting belt that connects the pair of anchor parts and provided on the inner side surface sides of the first and second support belts; and it can, with or without the center connecting belt, be equipped with a pair of operation belts respectively connected to the end portions of the first and second support belts.

In the lower back supporter of the present invention, when the anchor parts are put on the lower back, the inner side surfaces of the anchor parts closely contacts the skin of a wearer and does not slide, and the anchor parts play a role of anchor tape of conventional taping; and in addition, the first and second support belts that are connected to and fastened to that anchor parts have a role of a support tape of conventional taping. In addition, by wearing the supporter with slight tensile force applied by the anchor belts, the anchor belts play a role of securing a close contact of the anchor parts' inner side surface with the skin of the wearer and of eliminating the slippage. However, the anchor belts can be omitted. With the above-described structure, the lower back supporter of the present invention functions the same way as conventional taping and provides pressure, support, restriction and immobilization of the lower back, and it disperses the impact applied to the lower back and reduces and prevents recurrence of lower back pain; and it can be used instead of conventional taping.

The lower back supporter of the present invention is not directly put on the skin of a wearer using adhesive agent; accordingly, no concern of rash occurring on the skin of a wearer is required. Also, the same lower back supporter can be used any number of times, and it is less expensive than conventional taping. Furthermore, though it is necessary in conventional taping to rely on an expert when it is put on, the lower back supporter of the present invention can be easily worn by the patient just like conventional supporters; and after having it put on, if there is a sense of discomfort such as restriction, pressure or the like, it can be easily removed and then put back on, which is advantageous.

Furthermore, compared to the conventional lower back supporter, there is little pressure on the abdomen of the wearer, and thus it is possible to wear it for a long time, and slippage during wearing or the like is less likely to occur.

BRIEF DESCRIPTION OF THE SEVERAL VIEWS OF THE DRAWINGS

FIG. 3 shows the lower back supporter, seen from the abdominal side, in the process of being put on;

FIG. 4 shows the lower back supporter, seen from the back side, in the process of being put on;

DETAILED DESCRIPTION OF THE INVENTION

In the below, the lower back supporter of the present invention will be described in a more specific manner while referring to FIG. 1 through FIG. 10.

Figure 1:
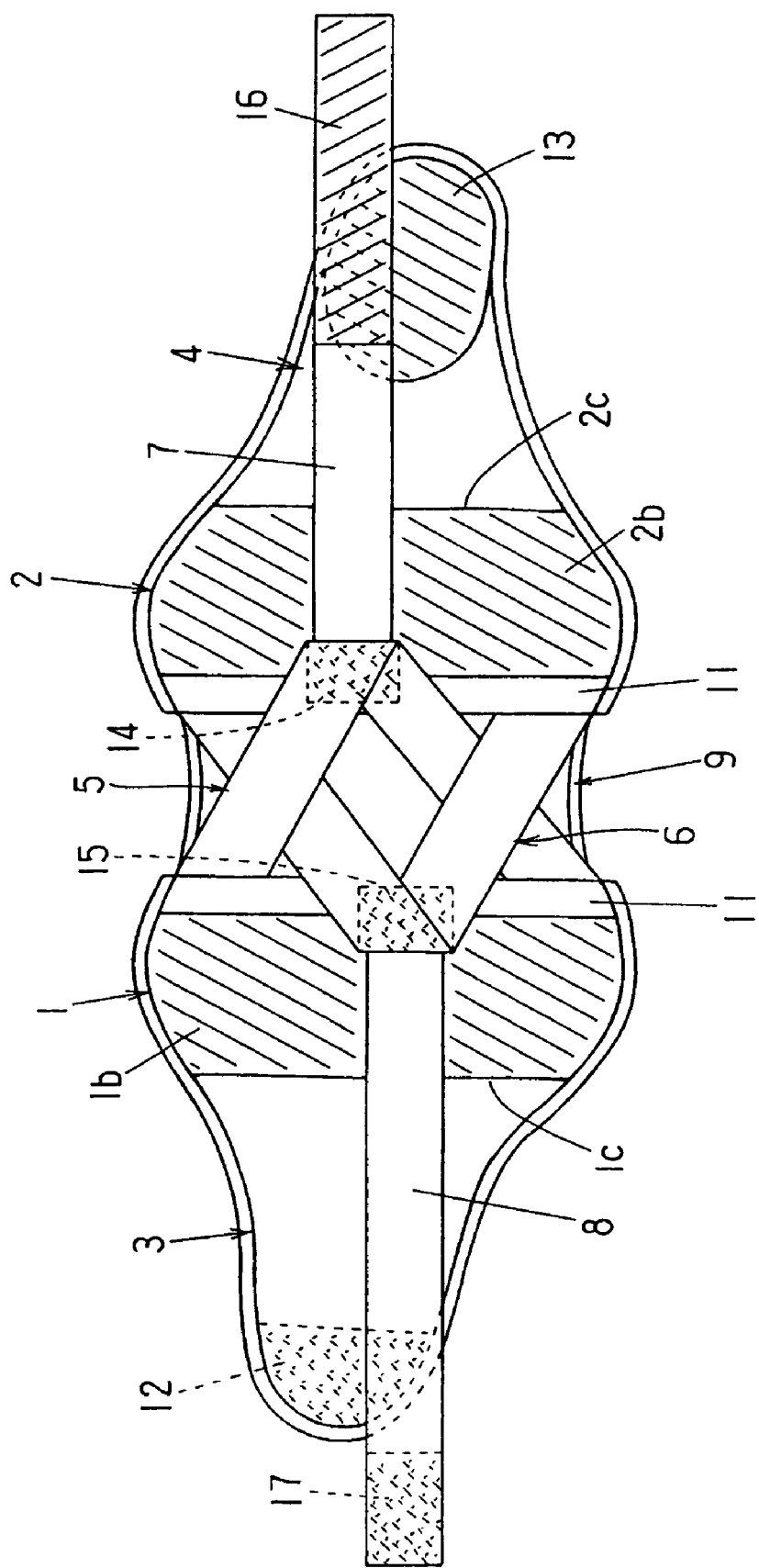
FIG. 1 shows the outer side of the lower back supporter of the present invention.
Figure 2:
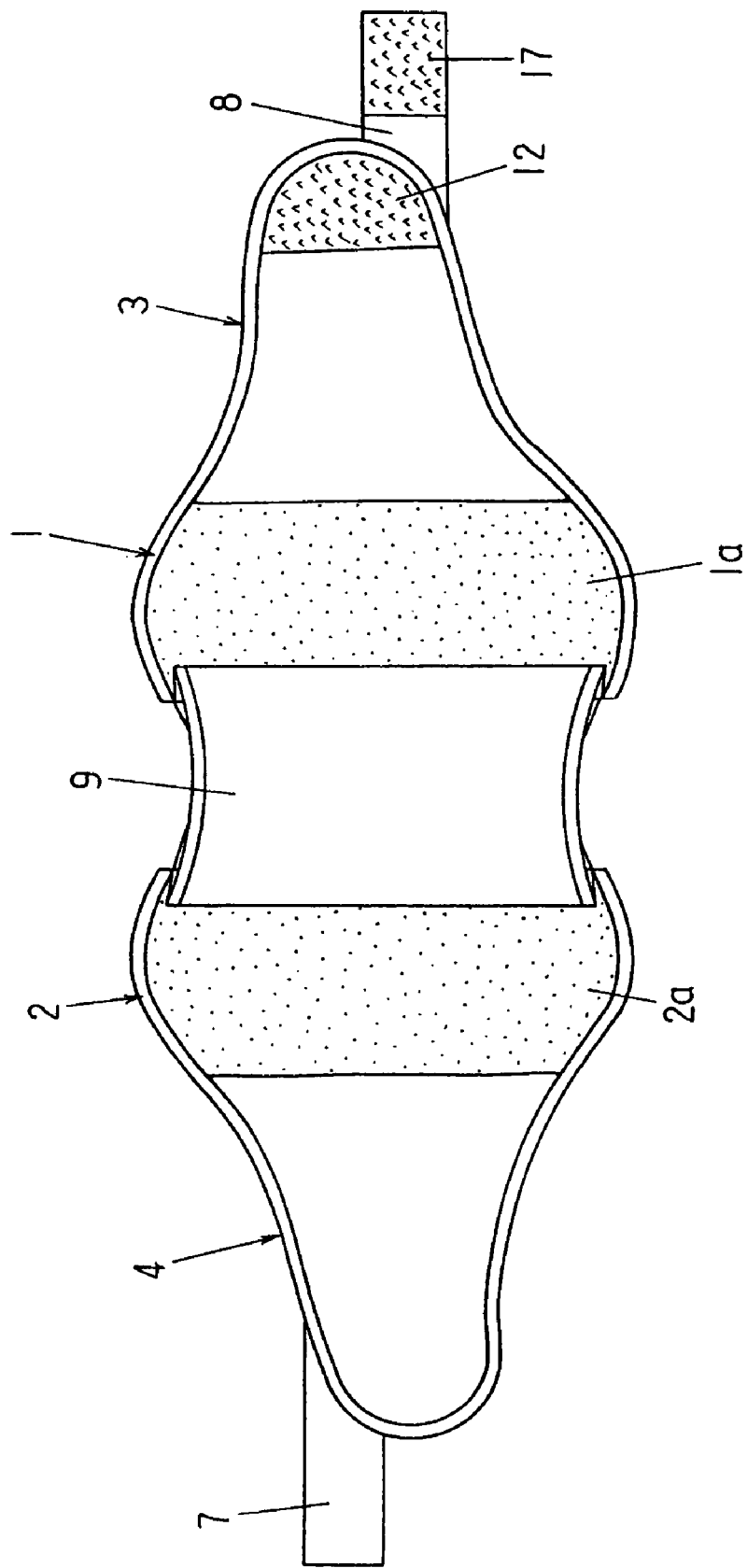
FIG. 2 shows the inner side of the lower back supporter.

The lower back supporter shown in FIGS. 1 and 2 is comprised of a pair of anchor parts 1 and 2 arranged with a specified space in between and anchor belts 3 and 4 connected respectively to the anchor parts 1 and 2; and it is further comprised of a first support belt 5, which is connected to the anchor part 1 and brought to the anchor part 2 via the central back side of the lower back and fastened to the outer side surface of the anchor part 2, and a second support belt 6, which is connected to the anchor part 2 and brought to the anchor part 1 via the central back side of the lower back and fastened to the outer side surface of the anchor part 1. Operation belts 7 and 8 are respectively connected to the first and second support belts 5 and 6, and a connecting belt 9 is provided between the anchor parts 1 and 2 so as to connect the anchor parts 1 and 2.

The inner side surfaces (areas 1a and 2a shown by the dots in FIG. 2) of the anchor parts 1 and 2 are comprised of a material that can closely contact the skin of a wearer and does not slip easily. Preferable materials include, among others, a foam resin (foam urethane resin or the like) and silicon rubber. The outer side surfaces (areas 1b and 2b shown by the diagonal lines in FIG. 1) of the anchor parts 1 and 2 consist almost entirely of a material to which a surface fastener can be fastened such as pile fabric or the like. Stays 11, which are hard and narrow in width, are attached to the inside edges (edge portions toward the center) of the anchor parts 1 and 2. Except for the stays 11, the anchor parts 1 and 2 as a whole consist of a flexible material. In addition, except for the stays 11, the anchor parts 1 and 2 as a whole have a stretchability derived from the elasticity. The anchor parts 1 and 2, nonetheless, do not need to have the ability to stretch.

The pair of anchor parts 1 and 2 are provided so that they have a space between them and have their horizontal width so that the anchor parts 1 and 2 are, when the lower back supporter is put on a wearer, in contact with a suitable lateral position extending from both sides of the waist toward the back of the wearer, preferably from the center point of each side of the body to the back side in the waist area of the wearer. For the vertical length of the anchor parts 1 and 2, a suitable length is selected so that the anchor parts 1 and 2 provide sufficient coverage vertically for the site of soreness as the center; and for the horizontal width, such width is selected so that the coverage necessary to ensure a close contact of the inner side surface of the anchor parts 1 and 2 with the skin of the wearer is assured (so that the supporter is prevented from slipping when tensile force is applied to the supporter from the first and second support belts 5 and 6 or when the wearer bends his body, for example).

The anchor belt 3 is sewn at its base part onto the outside edge (referred to by 1c) of the anchor part 1, and a surface fastener 12 (shown by the check marks in FIG. 2) is attached to the inner side surface of its end portion. On the other hand, the anchor belt 4 is sewn at its base part onto the outside edge (referred to by 2c) of the anchor part 2, and a receiving piece 13 (shown by the diagonal lines in FIG. 1) to which the surface fastener 12 of the anchor belt 3 is fastened is attached to the outer side surface of its end portion. The anchor belts 3 and 4 consist entirely of a flexible material and have stretchiness (elasticity). The anchor belts 3 and 4 preferably have stretchiness that can release the pressure on the abdomen when the lower back supporter is put on. Nonetheless, it is not essential for the anchor belts 3 and 4 to have stretchiness.

The first and second support belts 5 and 6 consisting of a flexible material are respectively formed substantially in a V shape. The base parts (open side of the V shape) of the first support belt 5 is sewn onto the inside edge (inside of the stay 11) of the anchor part 1, and a surface fastener 14 which fastens to the outer side surface 2b of the anchor part 2 is attached to the inner side surface of the pointed end portion (bottom of the V shape). On the other hand, the base parts (open side of the V shape) of the second support belt 6 is sewn onto the inside edge (inside of stay 11) of the anchor part 2, and a surface fastener 15 which fastens to the outer side surface 1b of the anchor part 1 is attached to the inner side surface of the pointed end portion (bottom of the V shape). With the stays 11 in between, the tensile force from the first and second support belts 5 and 6 is distributed almost evenly over the entire anchor parts 1 and 2 as a whole. The reason for making the support belts 5 and 6 substantially V-shape is to allow these belts to cross over in opposite directions to avoid interference with each other and to apply tensile force as evenly as possible to the anchor parts 1 and 2. Nonetheless, it is not essential that the support belts 5 and 6 be in substantially a V-shape.

Furthermore, the operation belt 7 is connected at its base part to the pointed end portion of the first support belt 5, and a receiving piece 16 fastened to a surface fastener is attached to the outer side surface of the end portion of the operation belt 7. On the other hand, the operation belt 8 is connected at its base part to the pointed end portion of the second support belt 6, and a surface fastener 17 fastened to the receiving piece 16 of the operation belt 7 is attached to the inner side surface of the end portion of the operation belt 8.

The V-shaped first and second support belts 5 and 6 have stretchiness of relatively strong elasticity. If the focus is on resting of the lower back when wearing the lower back supporter, then the first and second support belts 5 and 6 can be formed without the stretchiness; however, if movement of the lower back is desired, then elastic belts can be employed for them. Either type may be selected according to the purpose; however, it is generally preferable that the first and second support belts 5 and 6 have a certain amount of stretchiness to meet both demands.

The operation belts 7 and 8 are held by hands when putting the lower back supporter on; and they are used to pull the first and second support belts 5 and 6 laterally, and they do not have elasticity (stretchiness). More specifically, these operation belts 7 and 8 are provided to improve the operability in pulling the first and second support belts 5 and 6 laterally, and the presence or absence of stretchiness is not essential. However, it is somewhat preferable that the operation belts 7 and 8 do not have stretchiness so that pulling force is transmitted directly to the first and second support belts 5 and 6 as noted above. In the present invention, the operation belts 7 and 8 are not essential elements.

The connecting belt 9 is provided to prevent the anchor parts 1 and 2 from being separated, and they improve the operability of the lower back supporter when it is put on or stored. Thus, the connecting belt 9 is comprised of a flexible material and has stretchiness (elasticity). However, the presence or absence of stretchiness in the connecting belt 9 is not essential. With elasticity, it is possible for the connecting belt 9 to function so as to provide pressure and immobilization, and thus it is generally preferable that the connecting belt have stretchiness. The material of the connecting belt 9 can be the same as that of the anchor belts 3 and 4. The connecting belt 9 is, nonetheless, not an essential element.

Figure 3:
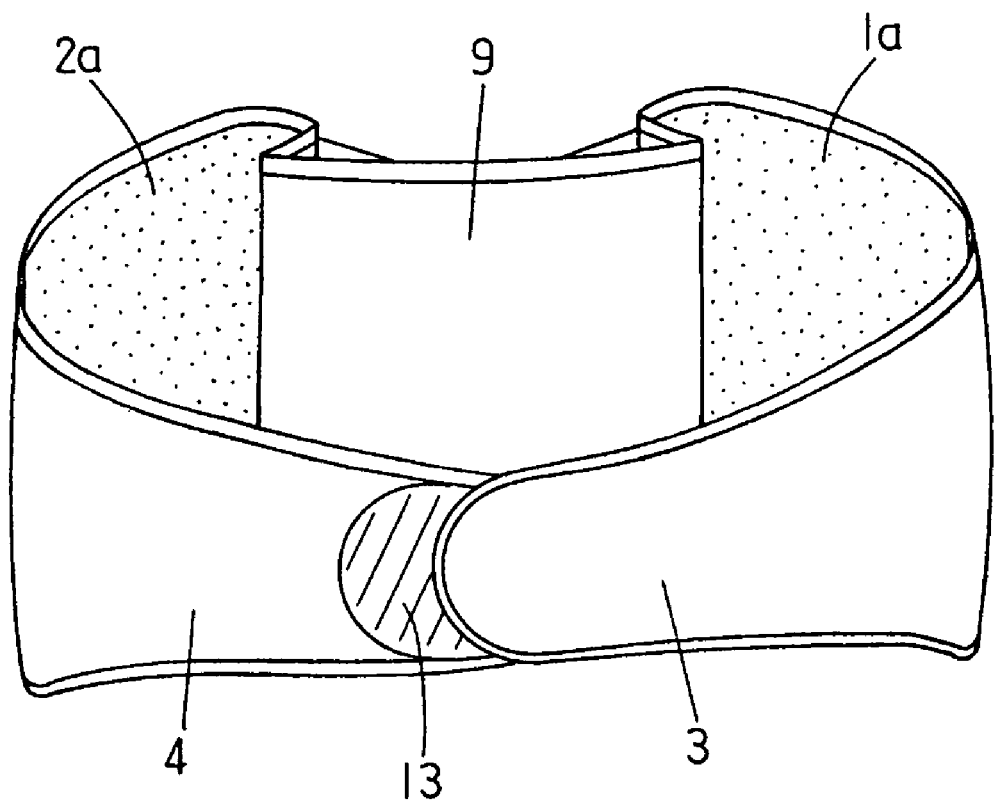
Figure 4:
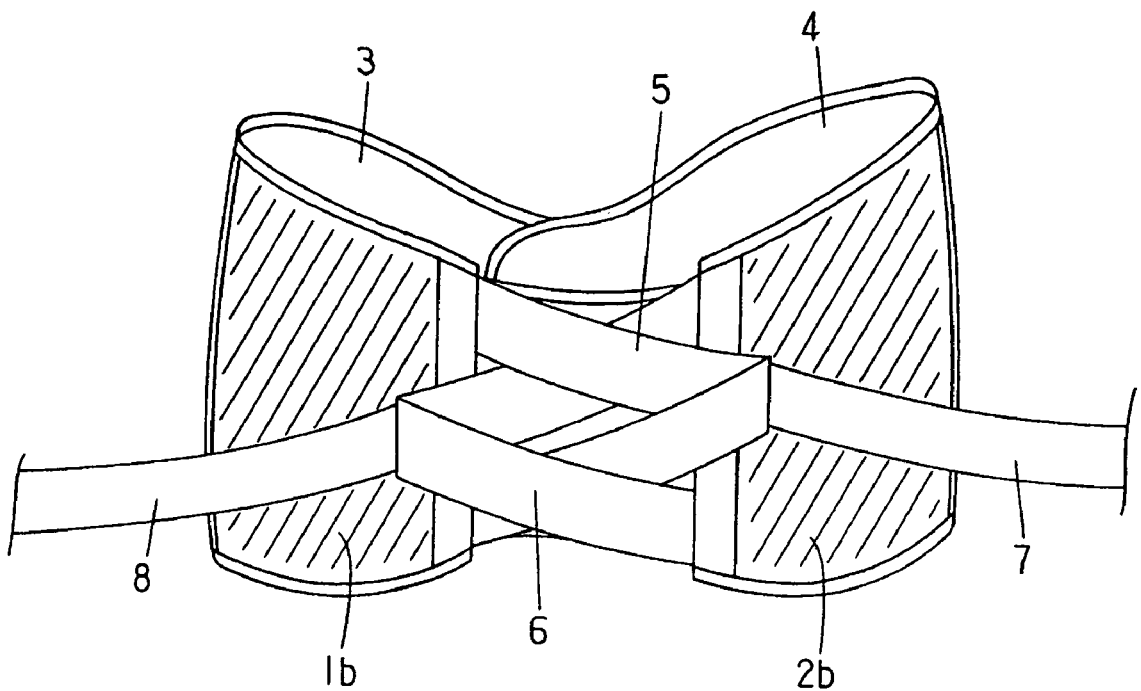

Next, referring to FIG. 3 to FIG. 6, the procedure for putting on the lower back supporter shown in FIGS. 1 and 2 will be described. First, holding the anchor belts 3 and 4, the anchor parts 1 and 2 are fitted almost symmetrically on the left and right sides of the lumbar spine, and the inner side surfaces 1a and 2a of the anchor parts 1 and 2 are brought into a close contact with the skin of both sides of the lumbar spine; then while lightly applying pulling force, the anchor belts 3 and 4 are wrapped around the abdomen side, and the surface fastener 12 of the anchor belt 3 is fastened to the receiving piece 13 of the anchor belt 4 so that the supporter is secured around the waist. At this time, as shown in FIGS. 3 and 4, the anchor parts 1 and 2 are at positions ranging from the center point of each side of the body to the back side in the waist area.

Figure 5:
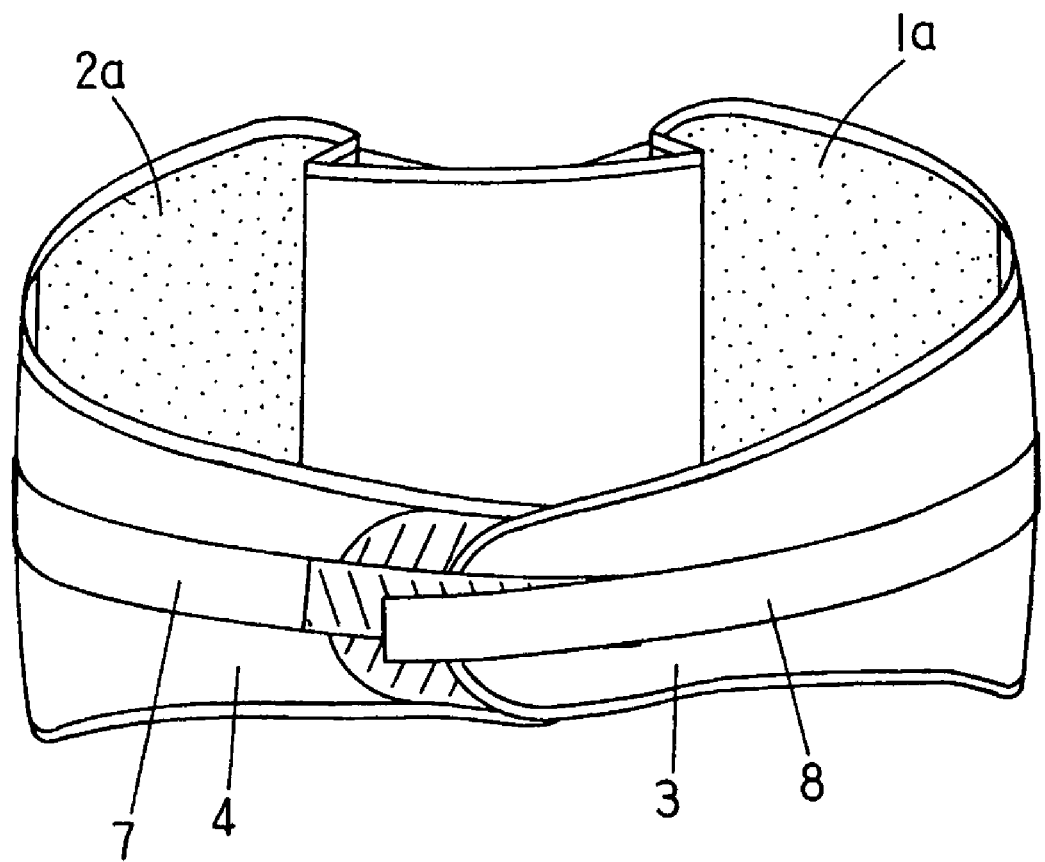
FIG. 5 shows the lower back supporter, seen from the abdominal side, in the state that it is worn.
Figure 6:
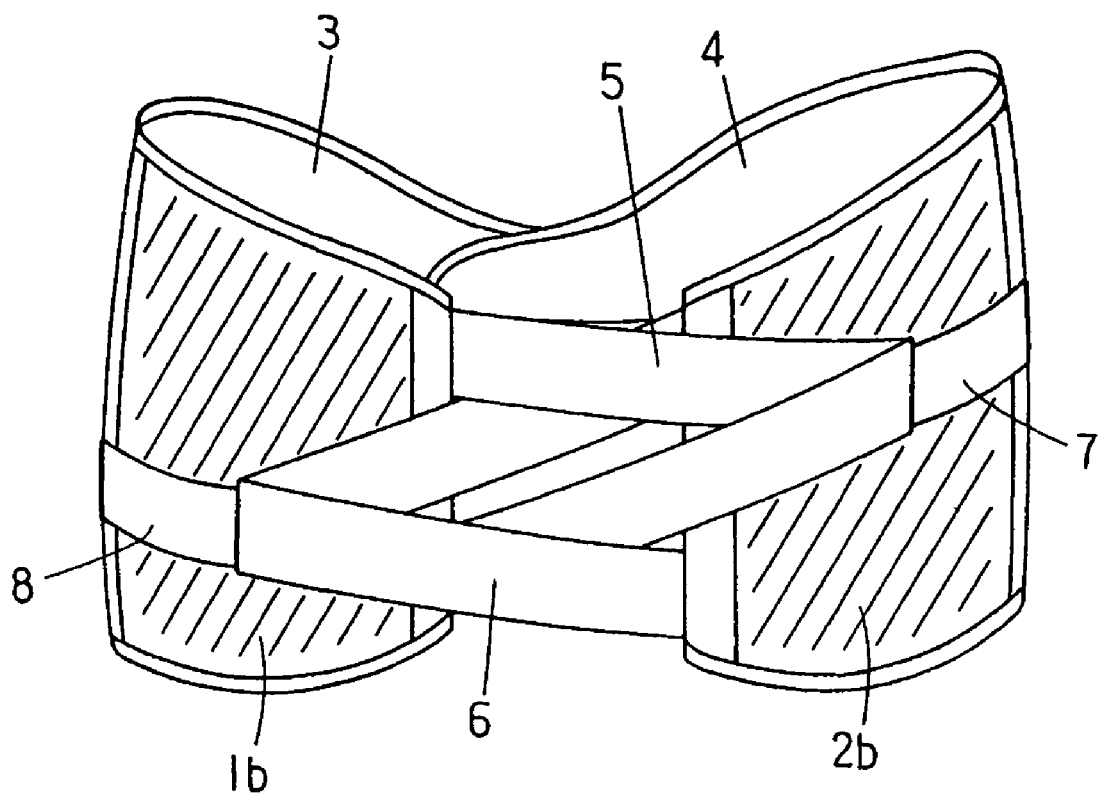
FIG. 6 shows the lower back supporter, seen from the back side, in the state that it is worn.

Next, holding the operation belts 7 and 8 with both hands, the operation belts 7 and 8 are pulled left and right to apply tensile force to the support belts 5 and 6; and then the surface fastener 14 of the end portion of the support belt 5 is fastened to the outer side surface 2b of the anchor part 2, and the surface fastener 15 of the end portion of the support belt 6 is fastened to the outer side surface 1b of the anchor part 1; and further the operation belts 7 and 8 are brought to the front (the abdomen side), and the surface fastener 17 of the operation belt 8 is fastened to the receiving piece 16 of the operation belt 7 (at this time, it is not necessary to apply tensile force to the operation belts 7 and 8). This state is shown in FIGS. 5 and 6. In the shown example, because the tensile force by the support belts 5 and 6 is being applied to the anchor parts 1 and 2, the space between the left and right anchor parts 1 and 2 is somewhat narrower (the skin of the wearer under the anchor parts 1 and 2 is pulled toward the center).

When the lower back supporter is not provided with the operation belts 7 and 8, the wearer holds the support belts 5 and 6 in hands and fastens the surface fasteners 14 and 15 thereof to the outer side surfaces 1b and 2b of the anchor parts 1 and 2.

When the lower back supporter is put on in this way, the anchor parts 1 and 2 contact closely to the skin of the wearer and slipping does not occur, and also tensile force is applied between the anchor parts 1 and 2 by the support belts 5 and 6; accordingly, it is possible to pressurize, support, restrict and immobilize the lower back area in the same manner as with conventional taping. In the above-described example, the tensile force by the support belts 5 and 6 is applied between the anchor parts 1 and 2; however, when the elasticity of the belt constituting the support belts 5 and 6 is great, or when there is no elasticity and they do not have stretchiness, the movement of the lower back is restricted even without applying the tensile force, functioning the same manner as taping.

Also, since the anchor belts 3 and 4 are wrapped around the abdomen, it is possible to prevent falling or slipping of the anchor parts 1 and 2 with just a very light application of tensile force to the anchor belts 3 and 4, and there is very little burden on the abdomen even when the supporter is worn for a long time. In other words, if a strong tensile force is applied by the support belts 5 and 6 between the anchor parts 1 and 2, or a strong tensile force is applied to the anchor parts 1 and 2 via the support belts 5 and 6 when the wearer bent his body, because the anchor parts 1 and 2 are in close contact with the skin of the wearer, strong tensile force is not applied to the anchor belts 3 and 4. Conventional lower back supporters increase the abdominal pressure so as to stabilize the lower back; however, as can be understood from the description above, the lower back supporter of the present invention does not increase abdominal pressure when stabilizing the lower back. In particular, in the example described above, the anchor parts 1 and 2 are set so that they are located from the center point of each side of the body to the back side in the waist area; accordingly, the burden on the abdomen is very small. However, portions of the anchor parts 1 and 2 can be positioned, without any problem, further frontward from the center points of both sides of the waist (which would increase the burden slightly on the abdomen), and the anchor parts 1 and 2 can be provided with a specified space in between on the left and right sides of the lumbar spine in the area ranging from both sides of the lower back to the back side.

Figure 7:
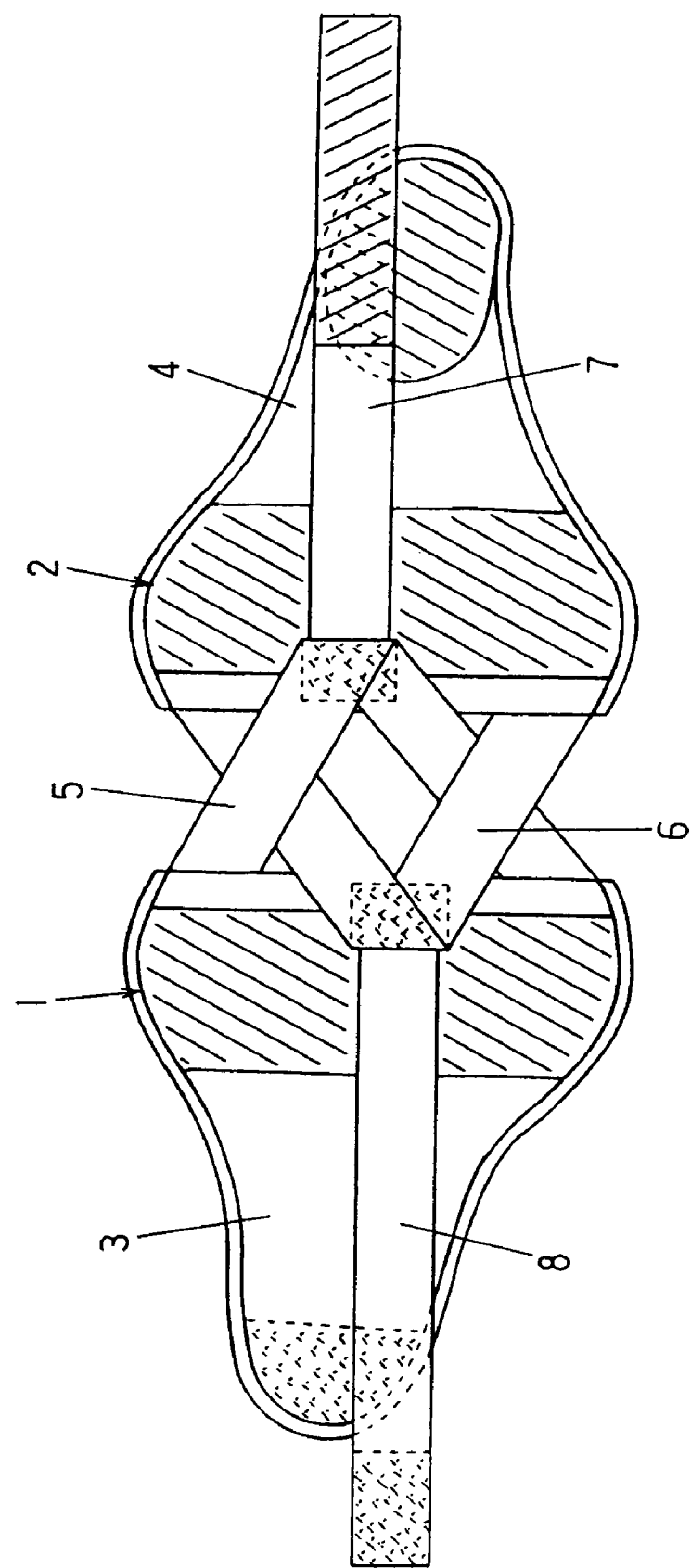
FIG. 7 shows the outer side of another lower back supporter of the present invention.
Figure 8:
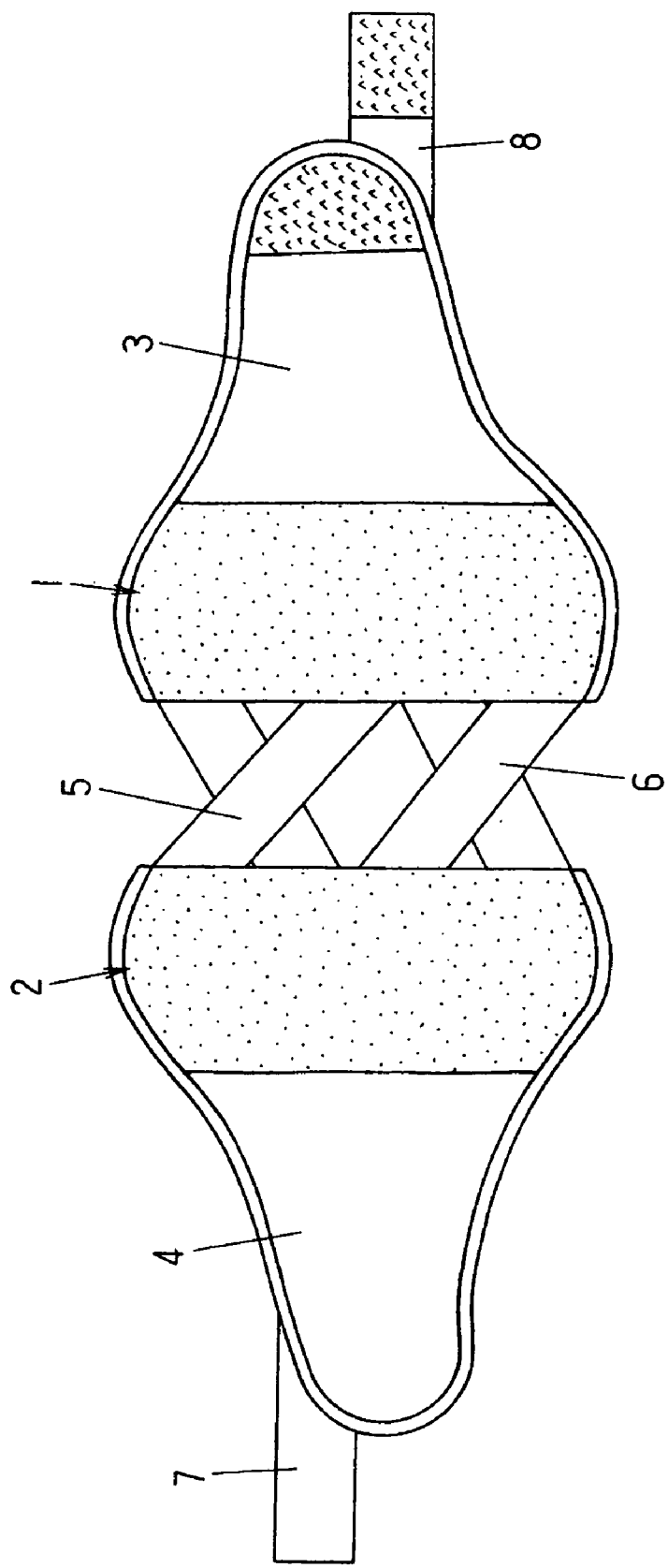
FIG. 8 shows the inner side thereof.

FIGS. 7 and 8 show a lower back supporter that is different from the lower back supporter shown in FIGS. 1 and 2 in that it is not provided with the connecting belt 9. Other components are the same as those of the supporter of FIGS. 1 and 2, and the method of putting it on is substantially the same. Because there is no connecting belt 9, the anchor parts 1 and 2 of the supporter of FIGS. 7 and 8 are not connected; however, since the substantially V-shaped support belts 5 and 6 cross over each other and are engaged, the anchor parts will not be completely separated from each other, and there is little trouble with handling. Nonetheless, it has an advantage that the structure is simpler because there is no connecting belt.

Figure 9:
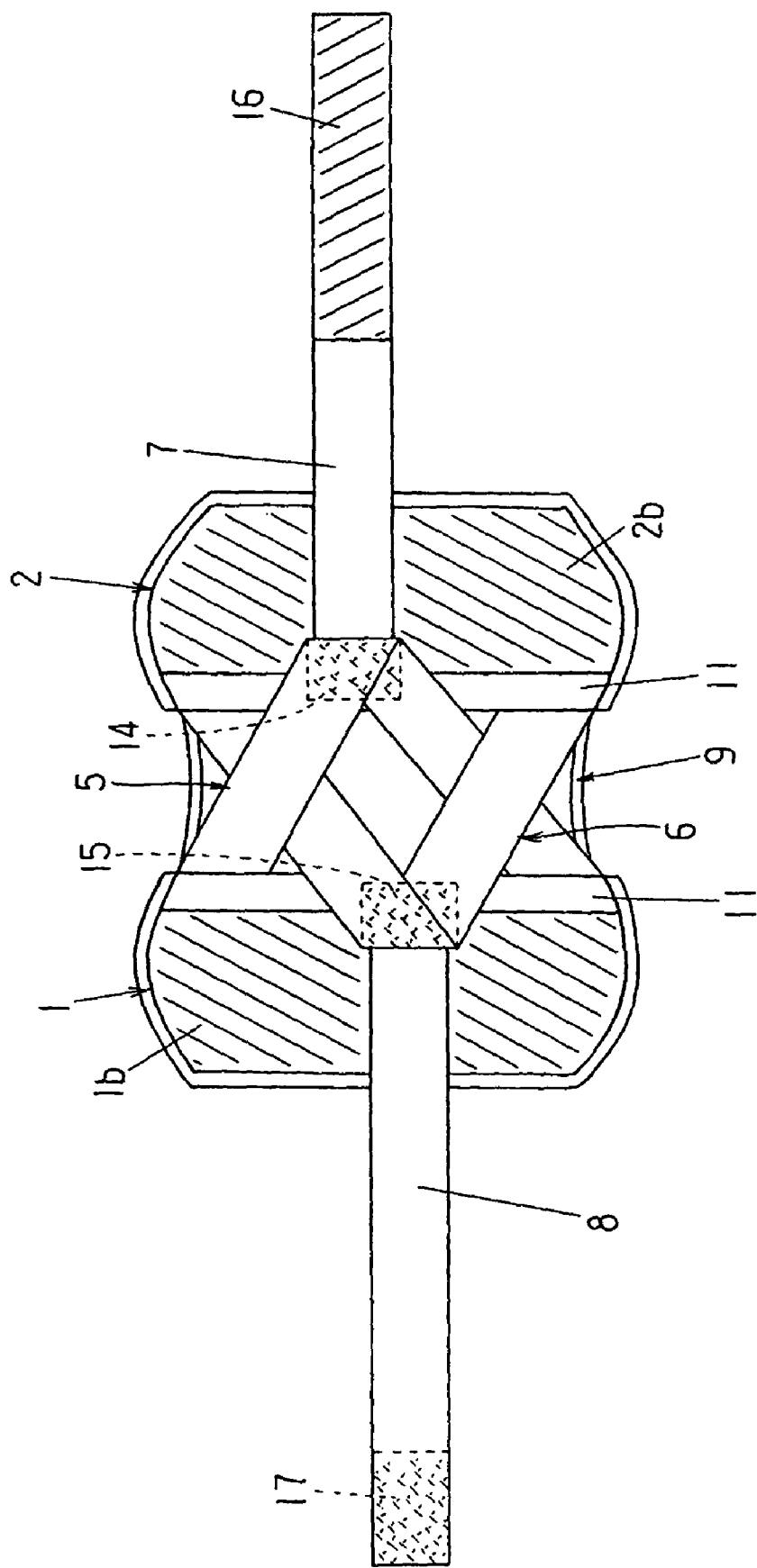
FIG. 9 shows the outer side of yet another lower back supporter of the present invention.
Figure 10:
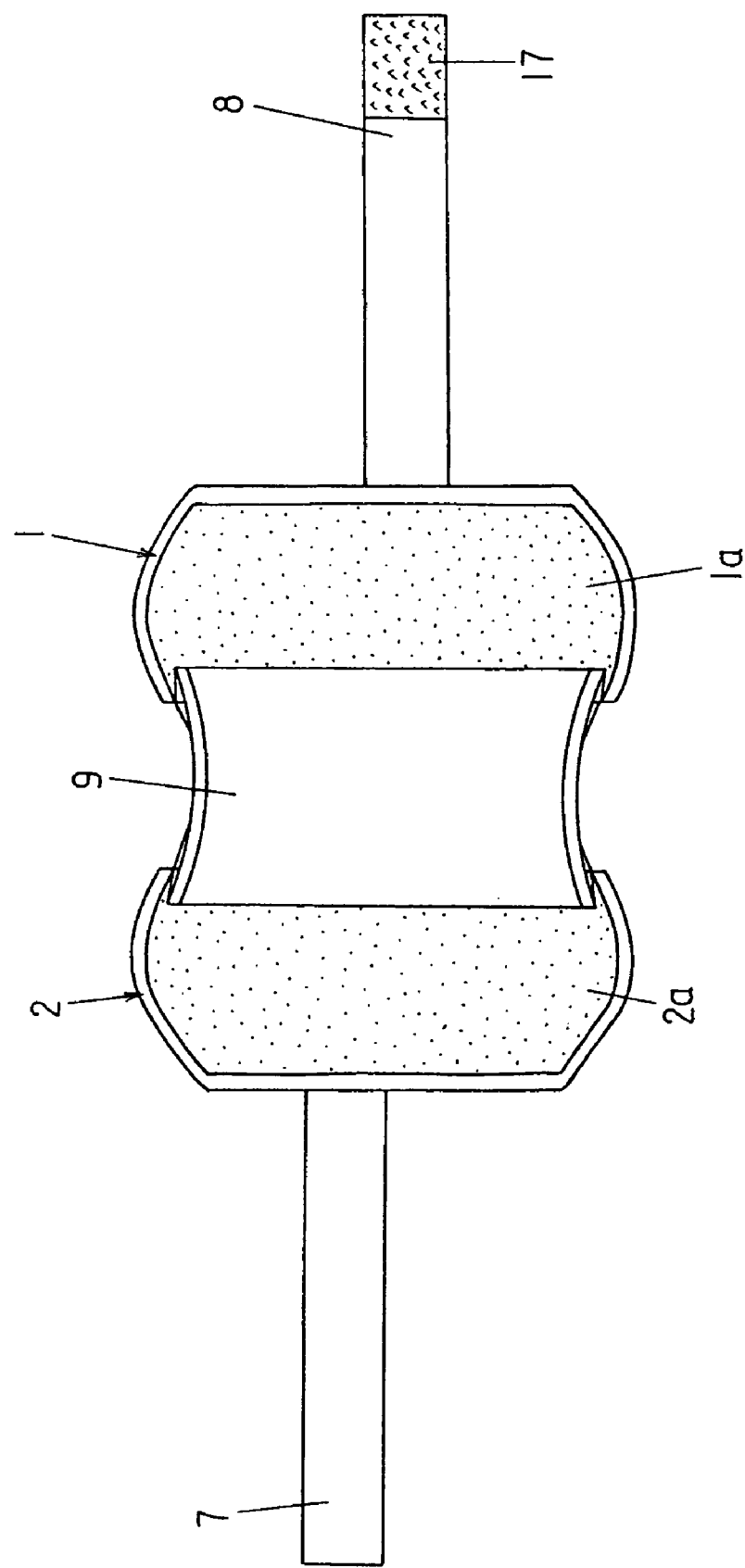
FIG. 10 shows the inner side thereof.

The lower back supporter shown in FIGS. 9 and 10 differs from the lower back supporter shown in FIGS. 1 and 2 in that it is not provided with anchor belts 3 and 4, and the other components are the same those of the supporter of FIGS. 1 and 2. Even without the anchor belts 3 and 4, by normally wearing clothing etc. (e.g. using a belt of a pants or a skirt), the anchor parts 1 and 2 can be held in place by being pressed by the belt, and slipping thereof does not occur easily. In addition, when, for example, a silicon rubber, which generally has a stronger contact to the skin of a wearer, is used for the material of the inner side surface 1a and 2a of the anchor parts 1 and 2, and when the shape of the anchor parts 1 and 2 is formed so that they can keep the three-dimensional shape that follows the shape of the lower back even when there is no burden thereon, it is possible to more reliably prevent slipping of the anchor parts 1 and 2.

The procedure for putting this lower back supporter on is the same as that in the lower back supporter shown in FIGS. 1 and 2 except that the anchor belt operation is not required. Since the lower back supporter is not provided with anchor belts, it is possible to eliminate the burden on the abdomen when wearing it.

Like the lower back supporter shown in FIGS. 1 and 2, it is possible to omit the connecting belt 9 and the operation belts 7 and 8.

The invention claimed is:
1. A lower back supporter comprising:
a pair of flat first and second anchor parts of which inner side surfaces comprising a non-slip material for closely contacting a skin of a wearer and of which outer side surfaces comprising a material to which first and second surface fasteners are respectively fastened, said pair of anchor parts configured to come into contact with a lower back of the wearer with a specified space in between;

a pair of anchor belts connected respectively to said pair of anchor parts and capable of being brought to an abdomen side of the wearer so that end portions of said anchor belts are coupled to each other;

a first support belt connected to said first anchor part and configured for being brought to said second anchor part through a central back side so that said first support belt is capable of being fastened to the outer side surface of said second anchor part via said first surface fastener;

a second support belt connected to said second anchor part and configured for being brought to said first anchor part through the central back side so that said second support belt is capable of being fastened to the outer side surface of said first anchor part via said second surface fastener; and a pair of operation belts respectively connected to end portions of said first and second support belts.

2. The lower back supporter according to claim 1, further comprising a center connecting belt that connects said pair of anchor parts, said connecting belt being provided on the inner surface side of said first and second support belts.

3. The lower back supporter according to claim 1, wherein the non-slip material is selected from the group consisting of foam resin and silicone rubber.

4. A lower back supporter comprising:

a pair of flat first and second anchor parts of which inner side surfaces comprising a non-slip material for closely contacting a skin of a wearer and of which outer side surfaces comprising a material to which first and second surface fasteners are respectively fastened, said pair of anchor parts configured to come into contact with a lower back of the wearer with a specified space in between;

a first support belt connected to said first anchor part and configured for being brought to said second anchor part through a central back side so that said first support belt is capable of being fastened to the outer side surface of said second anchor part via said first surface fastener;

a second support belt connected to said second anchor part and configured for being brought to said first anchor part through the central back side so that said second support belt is capable of being fastened to the outer side surface of said first anchor part via said second surface fastener; and a pair of operation belts respectively connected to end portions of said first and second support belts.

5. The lower back supporter according to claim 4, further comprising a center connecting belt that connects said pair of anchor parts, said connecting belt being provided on the inner surface side of said first and second support belts.

6. The lower back supporter according to claim 4, wherein the non-slip material is selected from the group consisting of foam resin and silicone rubber.

* * * * *